(12) United States Patent
Clarkson et al.

(10) Patent No.: US 10,130,560 B2
(45) Date of Patent: Nov. 20, 2018

(54) BIOACTIVE "SMART" DENTAL COMPOSITE MATERIALS

(71) Applicant: THE REGENTS OF THE UNIVERSITY OF MICHIGAN, Ann Arbor, MI (US)

(72) Inventors: Brian H. Clarkson, Ann Arbor, MI (US); Timothy F. Scott, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 3 days.

(21) Appl. No.: 15/127,041

(22) PCT Filed: Mar. 20, 2015

(86) PCT No.: PCT/US2015/021644
§ 371 (c)(1),
(2) Date: Sep. 19, 2016

(87) PCT Pub. No.: WO2015/143258
PCT Pub. Date: Sep. 24, 2015

(65) Prior Publication Data
US 2017/0172854 A1    Jun. 22, 2017

Related U.S. Application Data

(60) Provisional application No. 61/968,061, filed on Mar. 20, 2014.

(51) Int. Cl.
| | |
|---|---|
| A61K 6/00 | (2006.01) |
| A61K 6/093 | (2006.01) |
| A61C 5/00 | (2017.01) |
| C08K 3/36 | (2006.01) |
| C08K 3/32 | (2006.01) |
| C08F 2/38 | (2006.01) |
| C08F 2/48 | (2006.01) |
| A61K 6/083 | (2006.01) |

(52) U.S. Cl.
CPC .......... *A61K 6/0017* (2013.01); *A61K 6/0023* (2013.01); *A61K 6/0073* (2013.01); *A61K 6/083* (2013.01); *C08F 2/38* (2013.01); *C08F 2/48* (2013.01)

(58) Field of Classification Search
USPC .................. 523/116, 118, 122; 433/228.1
See application file for complete search history.

(56) References Cited

U.S. PATENT DOCUMENTS

| | | | | |
|---|---|---|---|---|
| 8,445,558 | B2 * | 5/2013 | Karim | A61K 6/083 433/218 |
| 2004/0171471 | A1 * | 9/2004 | Norenberg | A23G 4/064 501/1 |
| 2007/0185230 | A1 | 8/2007 | Bowman et al. | |
| 2010/0071846 | A1 | 3/2010 | Thiele et al. | |
| 2011/0144227 | A1 | 6/2011 | Bowman et al. | |
| 2012/0308622 | A1 | 12/2012 | Clarkson et al. | |
| 2013/0096219 | A1 * | 4/2013 | Bowman | C08F 2/00 522/33 |
| 2013/0123381 | A1 | 5/2013 | Bowman et al. | |

OTHER PUBLICATIONS

Ahn et al., Hexaarylbiimidazoles as visible light thiol-ene photoinitiators, Dent. Mater., 31(9):1075-89 (2015).
Scott et al., The design, development and evaluation of a nano/micro filled novel "smart" dental composite, 2014 AADR Annual Meeting, Charlotte, NC (presentation).

* cited by examiner

*Primary Examiner* — Tae H Yoon
(74) *Attorney, Agent, or Firm* — Marshall, Gerstein & Borun LLP

(57) ABSTRACT

Provided herein are composite materials comprising a thiol-ene polymer resin in a continuous phase and a filler in a discontinuous phase, the filler comprising fluorapatite crystals and silica. Further provided are methods of using these composite materials as restoratives in dental applications. This dental composite is labeled as "smart" because, when the shrinkage stress of the composite is greater than a programmable or pre-selected threshold level, it will elicit visual clues for the dentist.

16 Claims, 10 Drawing Sheets

Thiol-Ene Visible Light Photoinitiation

Conventional

- Camphorquinone/amine
- Irgacure 819 (BAPO)

Thiol-ene-specific

- Dihydroxy-hexaarylbiimidazole (HABI)

Chemical Composition of Solution For Fluorhydroxyapatite (FA) Formation
- 0.25 M EDTA-Ca-$Na_2$, 0.15 M $NaH_2PO_4$, 0.05 M NaF, pH 6.0
- Heat (121°C)
- Pressure (2 atm)
- Time (10 hrs)
FIG. 8
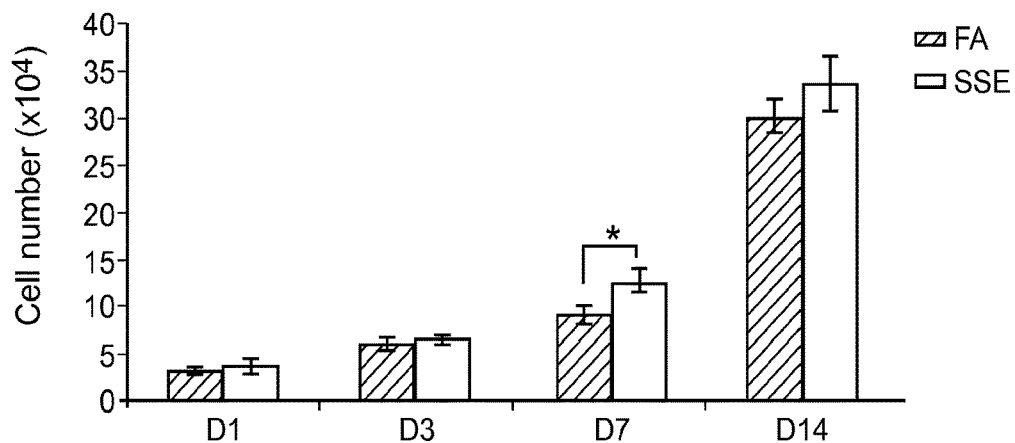
FIG. 9
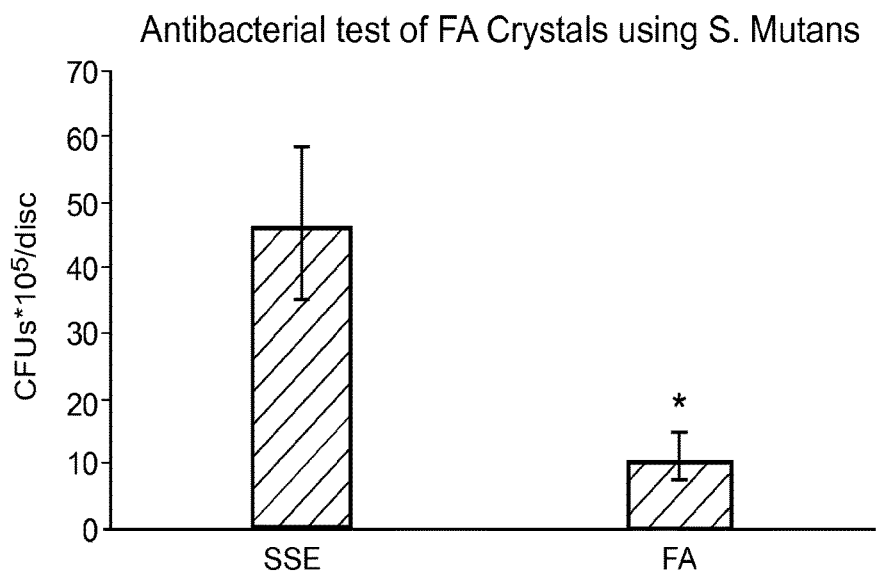
FIG. 10

- Most thermosetting reactions/processes lead to stresses of various amounts

BIOACTIVE "SMART" DENTAL COMPOSITE MATERIALS

CROSS REFERENCE TO RELATED APPLICATIONS

The benefit of U.S. provisional application No. 61/968,061, filed Mar. 20, 2014, is claimed, the disclosure of which is incorporated by reference in its entirety.

STATEMENT OF US GOVERNMENT SUPPORT

This invention was made with government support under grant number DE023771 awarded by the National Institutes of Health. The Government has certain rights in the invention.

BACKGROUND

Dental enamel is the outermost layer of the teeth. The fully developed mature dental enamel is made of enamel prisms, highly organized micro-architectural units, which have bundles of nanorod-like calcium hydroxyapatite (HA) crystals arranged roughly parallel to each other. This structure spans the entire enamel thickness and is likely to play an important role in determining the unique physico-chemical properties of the enamel.

Dental caries is a widespread, chronic, infectious disease experienced by almost 80% of children in the US by the age of 18 and by more than 90% of adults. Such a phenomenon is not restricted to the U.S., but rather is prevalent throughout the world. Caries is, in fact, considered to have a multifactorial etiology. The most prevalent way in which dentists treat carious tissue is to remove it surgically, resulting in an extensive cavity and loss of structural integrity of the tooth. The current standard of care for carious lesions in the dentin is invasive operative treatment. This means removal of all carious dentin (removal of all diseased tissue) and replacement by a restoration to restore form, function, and integrity of the tooth. The great number of such treatments also suggests that existing techniques have only limited success and that there will be an ongoing need for restoration of carious lesions, whether primary or secondary in nature. This operative treatment option is time-consuming to both dentists and patients, and costly. Worldwide, the placement, replacement, and repair of restorations in teeth account for anywhere from 30-70% of a dentist's activity. In order to reduce the cost of oral care to both the patient and governmental bodies, there is a need for the development of new anti-caries restorative products and materials.

Dentin hypersensitivity results when protective enamel or cementum covering dentine is lost. Cementum is easier to breach than enamel, because cementum is thinner and more easily eroded by acids. However, breach of cementum cannot happen until there is gingival recession and exposure of the root surface to the oral milieu. Individuals with breached cementum and suffering with dentinal hypersensitivity often experience pain when the exposed area of the tooth comes into contact with cold air or hot and cold liquids or foods that are sweet or acidic or is touched with a metal object.

One way that loss of cementum occurs (and the same is true of enamel) is by the process of dental caries. Acids are produced as end-products of the bacterial degradation of fermentable carbohydrate and these acids dissolve hydroxyapatite, which, like dentin and enamel, is the main calcium phosphate mineral that comprises most of the mineral of the cementum. Another source is acidic foods which, if ingested frequently and for prolonged periods of time, will cause tooth demineralization. These include fruit juices and many beverages, both alcoholic and non-alcoholic. Other acidic agents leading to chemical erosion include various oral personal care products. Amongst these are many of the commercially available mouthwashes and some toothpastes. Abrasive toothpastes and vigorous brushing can aid the erosion process. Another way in which dentin tubules lose their protective cementum and enamel coverings is through procedures performed by the dentist or hygienist in the dental office. This includes cavity and crown preparation of teeth for fillings and other restorations. It also includes cementum removal during scaling and root planing by the periodontist or dental hygienist.

Many attempts have been made with limited success to obstruct exposed dentinal tubules and to thereby reduce or stop the ability of stimuli to reach the pulp and cause pain. Materials either singly or in combination have been tried to produce an effective barrier. Blockage of the tubules through the formation of a calcium phosphate precipitate is a common approach. This includes the mixing of a soluble calcium salt with a soluble phosphate salt and immediately applying the combination to the open tubules. Alternatively, application of one salt before the other to try to get a precipitate to form within tubules is also used. There remains acute need for compositions and methods for blocking exposed dentinal tubules to treat dentinal hypersensitivity.

SUMMARY

Provided herein are dental composites, alternatively referred to as compositions throughout this disclosure. The dental composites comprise a resin of a thiol, an alkene, and optionally a spiropyran or spirooxazine, as disclosed herein. The composite also comprise a filler and a fluorapatite. These composites can be used in various dental applications as disclosed herein.

BRIEF DESCRIPTION OF THE FIGURES

FIG. 8 shows the makeup of fluorapatite (FA) and its preparation.

FIG. 9 shows growth of human gingival fibroblasts on two composites, the fluorapatite (FA) composite and non-coated stainless steel (SSE) disc (control) over 2 weeks.

FIG. 10 shows antibacterial tests on FA crystals using *S. mutans*.

DETAILED DESCRIPTION

Provided herein is a composite material comprising a continuous resin and discontinuous filler. The composite system includes both the continuous resin and discontinuous filler components, and the combination of these components into a robust, self-reporting, self-healing, and biomimetic composite dental restorative system. This dental composite is labeled as "smart" because, when the shrinkage stress of the composite is greater than a programmable or pre-selected threshold level, it will elicit visual clues for the dentist; and "semi-smart" because at low pH remineralizing ions will be released to help repair (e.g., it is self-healing) any demineralization of adjacent demineralized dental tissue. We propose the utilization of the radical-mediated, step-growth, thiol-ene polymerization mechanism, in conjunction with stress relaxation via network topology reconfiguration and molecular stress sensors.

The continuous resin can be a thiol-ene resin. The discontinuous filler portion comprises fluorapatite crystals and silica particles. Based upon preliminary studies, these FA crystals impart biological activity to yield an efficacious, resilient and robust composite dental restorative material.

Monomers contemplated in the preparation of thiol-ene resins for the disclosed composites include a thiol monomer and a alkene (e.g., a diene) monomer. One contemplated thiol is pentaerythritol tetra(3-mercaptopropionate) (PETMP). Contemplated alkenes include tri- or tetra-unsaturated moieties about a core, the unsaturated moieties comprising an allyl or norborenyl group, and the core comprising a trimethylolpropane, a pentaerythritol, a triazine, or a triazinetrione, as shown in Scheme 1B below. In some embodiments, one or more spiroheterocyclic monomers (e.g., allyl sulfide ring opening monomers) are also used (see Scheme 2 below) in the preparation of the thiol-ene resin. Some specific thiol-ene monomer combinations contemplated include tetramercaptoethylsilane (TMES) and triallyltriazinetrione (TATATO) (TMES/TATATO); tetramercaptopropylsilane (TMPS) and TATATO (TMPS/TATATO); TMES/TATATO/dinorbornyl bisphenol A (DNBPA); and TMES/TATATO/dinorbornyl tetramethyl cyclobutane (DNTCB).

Figure 6:
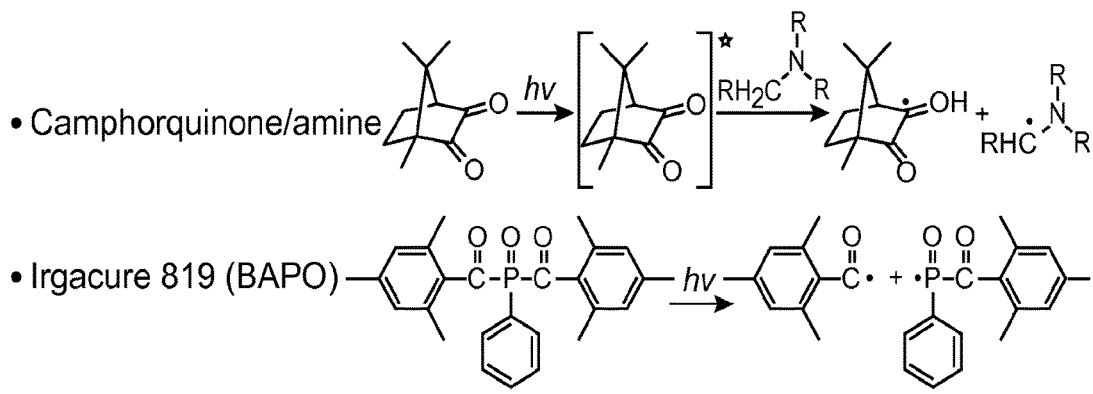
FIG. 6 shows various photoinitiators used in the thiol-ene polymerization.
Figure 6:
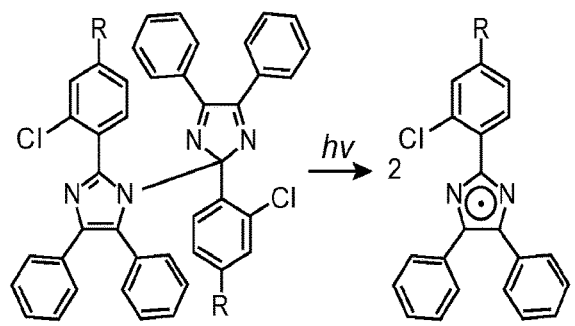
Figure 7:
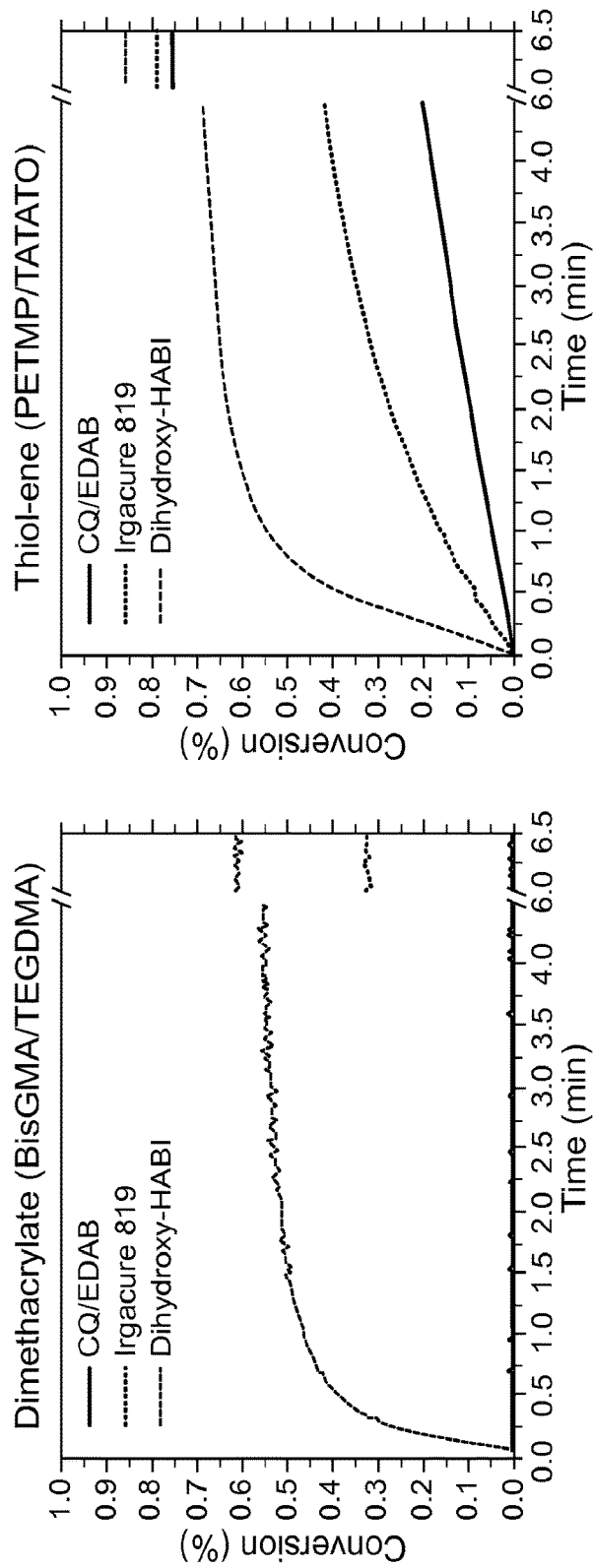
FIG. 7 shows photoinitiation of thiol-ene polymerization with various initiators.
Figure 7:
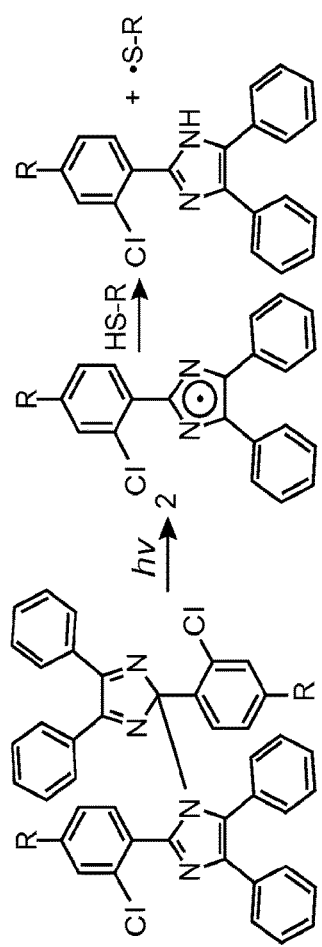
Figure 11:
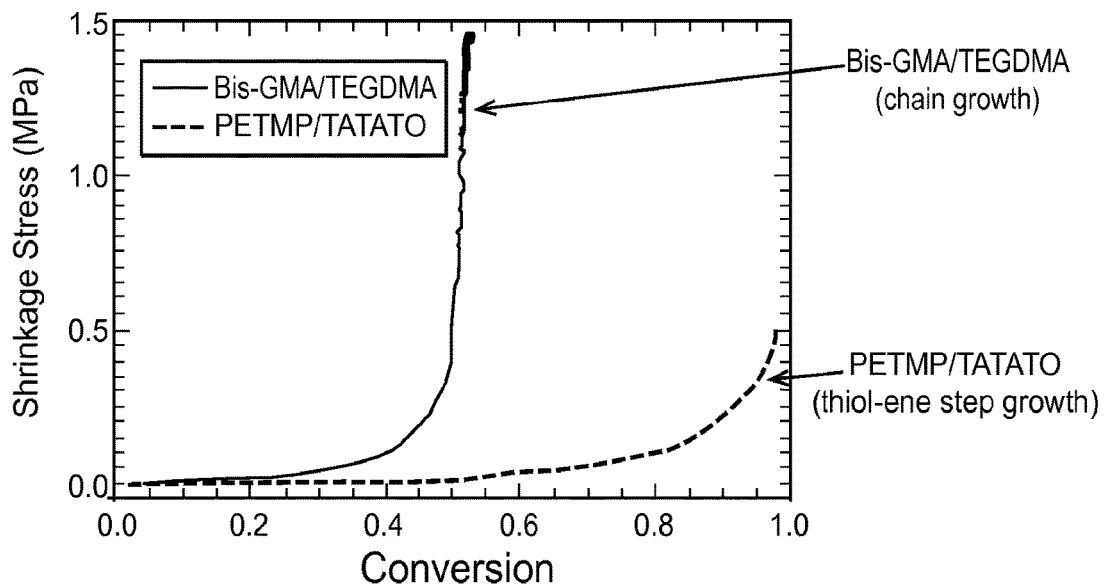
FIG. 11 shows comparison of shrinkage stress of two types of resins, indicating that the thiol-ene resin has vastly reduced polymerization-induced shrinkage stress compared to the typical Bis-GMA/TEGDMA resin used in dental applications.
Figure 12:
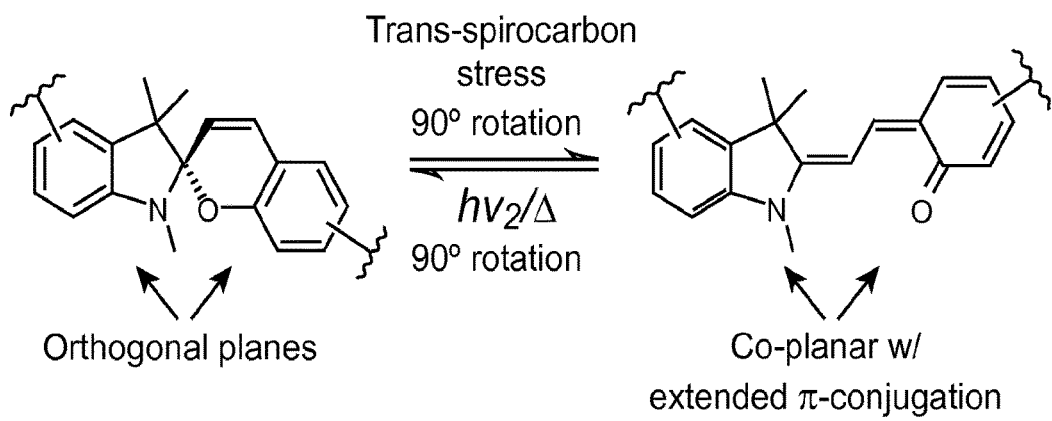
FIG. 12 shows spiropyrans and their rotation.

The resins can be prepared by mixture of the selected monomers in the presence of a photoinitiator. The initiator can be, e.g., BAPO, HBA, or HABI (see FIG. 6). In some cases, the photoinitiator is HABI.

Although significant research effort has been devoted to attaining low shrinkage and shrinkage stress in composite dental restoratives, formulation of composite resins that are both able to relax polymerization-induced shrinkage stress via rearrangement of the network topology and self-report the development of stress during polymerization have not previously been reported. Provided herein is a resin based upon a radical-mediated, step-growth thiol-ene polymerization mechanism, in conjunction with stress relaxation via addition-fragmentation chain transfer, to afford biocompatible polymeric resin phase that can exhibit low oxygen sensitivity, low extractable content, and low shrinkage stress, making it suitable for use in a dental material. In some embodiments, incorporation of spiroheterocyclic monomers is contemplated. These monomers can act as colorless molecular stress sensors that manifest visible cues to raised stresses, making them suited for self-reporting composite dental restorative materials.

Prior composite materials typically comprise silica-based particulate fillers dispersed in a cross-linked methacrylic continuous phase. The polymerization of these materials is typically accompanied by a significant amount of frustrated volumetric shrinkage and associated shrinkage stress, leading to a wide range of deleterious effects. (Meth)acrylates undergo a radical-mediated chain growth mechanism and can be thermally-initiated at raised temperatures or redox- or photo-initiated under ambient conditions. Unfortunately, these polymerizations are strongly inhibited by oxygen, leading to tacky surfaces due to incomplete surface polymerization. Additionally, the chain-growth mechanism often results in large amounts of unreacted, extractable monomer remaining after polymerization has ceased, potentially leading to acute toxicity or sensitization. In contrast, the thiol-ene polymerization mechanism avoids these disadvantages of methacrylate polymerization, owing to its combination of characteristics relative to other radical polymerization systems. Thiol-ene polymerizations proceed via a radical-mediated step growth mechanism between multifunctional thiol and non-homopolymerizable vinyl monomers, where a thiyl radical adds to a vinyl, which subsequently abstracts a hydrogen from a thiol, generating a thioether moiety and regenerating a thiyl radical (See FIGS. 1 and 3-5).

Interest in thiol-ene systems has recently renewed owing to their unique polymerization properties and a drive to develop toxicologically safer alternatives to acrylics. These systems demonstrate nearly all of the advantages of typical radical-mediated polymerizations in that they can polymerize rapidly, do not require solvents for processing, are optically clear, and provide an range of mechanical properties. Additionally, thiol-ene polymerizations proceed via a step-growth mechanism, display delayed gelation, enable radical polymerization of a wide range of thiol and vinyl functional group moieties, and form homogeneous polymer networks with narrow glass transition regions. Moreover, thiol-ene systems exhibit less shrinkage per mole of double bonds reacted, 12-15 $cm^3$/mol for thiol-enes compared to 22.5 $cm^3$/mol for methacrylates, leading to reduced polymerization shrinkage stress and improved substrate adhesion, compared to methacrylates. Thiol-ene polymerizations demonstrate resistance to oxygen inhibition, a consequence of hydrogen abstraction by the peroxy radical from the ubiquitous thiol.

There are several strategies for combating the deleterious effects of shrinkage stress in rapid free-radical polymerizations. One common mitigation approach is the minimization of polymerization shrinkage, achievable through a variety of means. Oligomeric polymerizable species have been used to reduce polymerization shrinkage and subsequent shrinkage as the concentration of reactive species is low. Additionally, ring-opening polymerizations, such as those employing epoxy or spiro compounds, and polymerization-induced micro-phase separation have shown potential to reduce shrinkage. However, upon full conversion to a chemical gel, there are few mechanisms to alleviate shrinkage stress without effecting irreversible network degradation.

The approach disclosed herein for achieving low shrinkage stress is different from these earlier techniques. In previous work, stress relaxation both during and post-polymerization has been demonstrated by the introduction of radical species into cross-linked polymer networks containing allyl sulfide functionalities. Incorporation of the allyl sulfide functionality into a chemical network allows for bond rearrangement via addition-fragmentation chain transfer. This reaction preserves the concentration of both the allyl sulfide and thiyl radical reactants, which subsequently participate in further addition-fragmentation events. This addition-fragmentation reaction cascade, where an active center effectively diffuses throughout the network, enables a global reduction in stress without concomitant network degradation.

Spiroheterocyclic monomers, e.g., spiropyran or spirooxazine compounds, are known for exhibiting photochromic behavior by undergoing a photo-induced, reversible transformation between two isomers having different absorption spectra. Recently, spiropyrans have been employed as 'mechanophores', species that, when incorporated in the backbone of polymeric materials and deformed, undergo stress-induced isomerization and effect the development of color and fluorescence. Incorporation of low concentrations of polymerizable mechanophores, mechanically-activated chromophores that manifest visible cues at raised stresses, in the resin phase of composite dental restoratives is contemplated to yield materials that can produce a transient visible signal localized to sections of the composite material where the shrinkage stress during polymerization exceeds a stress threshold but that are otherwise indistinguishable from existing systems. Although these molecular stress sensors are not specifically intended to reduce the stress accumulated in photopolymerized composite restoratives, their utilization yields self-reporting materials that allow practitioners (dentists) to determine localized stress levels, evaluate the efficacy of shrinkage stress-reduction strategies, and immediately assess dental restoration success, ultimately improving patient outcomes and increasing longevity of composite restorations by allowing dentists to recognize and then remove poorly placed composites.

As a major component of hard tissues such as bone and teeth, hydroxyapatite (HA) [$Ca_5(PO_4)_3(OH)$] has been of interest with regard to its physicochemical properties for various biomedical applications. However, the limited stability of HA with its thermal decomposition products, which are soluble in the body, has stimulated interest in bioactive materials with increased resorption resistance. One such material is fluorapatite (FA) [$Ca_5(PO_4)_3F$], within which the fluoride ions replace the hydroxyl ions of the HA to create a tighter lattice structure. This increases the stability and reduces the solubility of the FA. FA has been regaining attention and has been increasingly investigated in the last 10 years for its stimulating effects in hard tissue regeneration; and for the purpose of maintaining the stability of materials during processing. Consequently, the filler of the disclosed composite dental restorative materials comprises FA crystals, which are identical, or compatible, in shape and composition to the crystals in enamel. They can be produced, depending on the synthesis conditions, of various sizes from nano to micro scale. These crystals have been shown to have properties which are suited for incorporation as a filler in a dental composite. They are biocompatible with several cell types including gingival epithelial cells, dental pulp stem cells (DPSCs), osteoblast-like cells and others. Thus, as composite restoration are placed subgingivally, the incorporation of the FA crystals in the composite can assist in good gingival health and may, in fact, encourage adhesion of the gingival cells to the composite to produce a gingival seal. Gingival health may also be encouraged and sustained by the innate antibacterial nature of the FA crystals. *Porphyromonas gingivalis* is one of the known pathogens implicated in periodontal disease. The FA crystal coatings have already been shown to inhibit the growth of *P. gingivalis* and the FA crystal/silica-containing composites disclosed herein can be used to combat this oral pathogen.

The most vulnerable area of a composite restoration for caries to occur is at the interface of the tooth with the restoration. Caries is caused by pathogenic bacteria (*streptococcus mutants, lactobacillus*, etc.) which produce acids that can demineralize both enamel and dentin. The FA crystals, like enamel and dentin, at this low pH release calcium, phosphate, and fluoride which will help remineralize the demineralized area in a "self-healing" process. Naturally, for this self-healing to occur the FA crystals have to be exposed which would occur during the final finishing of a composite, which includes polishing. Since this ion release will only occur as the pH drops and then stop as the pH rises, any degradation of the composite itself is minimized. It should be noted that if demineralization (caries) of the tooth is not countered by this ion release from the composite the secondary caries will progress and eventually the composite will have to be replaced or, at least, repaired. The FA crystals have been shown to have an antibacterial effect on *Streptococcus mutans*.

There are also other implications for including the FA crystals in this new composite based on their effect on DPSCs. Not only are the FA crystals biocompatible to these cells but the crystals actually stimulate them to mineralize. Thus, in deep cavities (near pulp exposure or even pulp exposure) on placement of the FA/silica-filled composite material, the pulp would be encouraged to produce a mineralized barrier thus protecting the pulp from further and future injury. Once this barrier has formed no further mineralization would be expected because the FA crystals would not be in contact and/or close contact with the pulp tissue.

Finally, the present disclosure is not just to provide a new composite restorative material but provides a FA/silica filler in the resin as a material that, depending on its viscosity, can be used as a lining material, bonding agent, or sealant, affording a "one-box", biocompatible material that can be used in many dental restorative situations.

The composite material disclosed herein comprises thiolene-based "smart" polymer as its continuous phase, which features low shrinkage stress, not air inhibited, low extractable content, and mechanophoric self-reporting of stress. This polymer is filled in total with silanated silica particles or in part with fluorapatite crystals of nano to micro size that are similar in shape and composition to enamel crystals. These crystals impart a bioactivity to the filler particles in the areas of; epithelial/pulp cell biocompatibility, remineralization capabilities, and antibacterial activity. The polymer system is self-adhesive to eliminate the need for a separate bonding agent and to reduce technique sensitivity. The composite materials disclosed herein are assessed for proteolytic degradation, antibacterial activity against pathogenic oral bacteria, ion release and in vitro biocompatibility using appropriate cell lines, dental pulp stem cells, gingival fibroblasts and osteoblast-like cells. Mechanic properties of the disclosed composite materials include shrinkage vol. of the polymer of less than 8% and the composite less than 4% vol. or less than or about 1% vol.

The composite materials disclosed herein comprise a continuous resin and a discontinuous filler. The filler can comprise up to 50 wt % of the composite. Also contemplated is that the filler comprises about 0.1 wt % to about 50 wt %, about 0.1 wt % to about 45 wt %, about 0.1 wt % to about 40 wt %, about 0.1 wt % to about 35 wt %, about 0.1 wt % to about 30 wt %, about 0.1 wt % to about 25 wt %, about 0.1 wt % to about 20 wt %, about 0.1 wt % to about 15 wt %, about 0.1 wt % to about 10 wt %, about 0.1 wt % to about 5 wt %, about 5 wt % to about 50 wt %, about 10 wt % to about 50 wt %, about 15 wt % to about 50 wt %, about 20 wt % to about 50 wt %, about 25 wt % to about 50 wt %, about 30 wt % to about 50 wt %, about 35 wt % to about 50 wt %, about 40 wt % to about 50 wt %, or about 45 wt % to about 50 wt %, based upon the total weight of the composition.

Resins:

Resins disclosed herein can include a polymer prepared by a thiol-ene polymerization, e.g., a thiol-ene polymer. The resin can also comprise a spiropyran or spirooxazine, e.g., at concentrations of about 0.01 wt % to about 10 wt %, based upon the total weight of the resin. Also contemplated are concentrations of about 0.05 wt % to about 5 wt %, about 0.05 wt % to about 4 wt %, about 0.05 wt % to about 3 wt %, about 0.05 wt % to about 2 wt %, about 0.05 wt % to about 1 wt %, about 0.1 wt % to about 1 wt %, about 0.5 wt % to about 2.5 wt %, or about 0.1 wt % to about 2 wt %. In some cases, the resin comprises a spiropyran. In various cases, the resin comprises a spirooxazine.

Fillers:

The filler of the composite material comprises FA and silica particles. The FA can be about 10 wt % to about 90 wt % of the total filler weight. Also contemplated are about 10 wt % to about 80 wt %, about 10 wt % to about 70 wt %, about 10 wt % to about 60 wt %, about 10 wt % to about 50 wt %, about 10 wt % to about 40 wt %, about 10 wt % to about 30 wt %, about 10 wt % to about 20 wt %, about 20 wt % to about 90 wt %, about 30 wt % to about 90 wt %, about 40 wt % to about 90 wt %, about 50 wt % to about 90 wt %, about 60 wt % to about 90 wt %, about 70 wt % to about 90 wt %, about 80 wt % to about 90 wt %, about 20 wt % to about 80 wt %, about 30 wt % to about 80 wt %, about 40 wt % to about 80 wt %, or about 50 wt % to about 80 wt %, based upon the total amount of filler. The silica particles can be about 10 wt % to about 90 wt % of the total filler weight. Also contemplated are about 10 wt % to about 80 wt %, about 10 wt % to about 70 wt %, about 10 wt % to about 60 wt %, about 10 wt % to about 50 wt %, about 10 wt % to about 40 wt %, about 10 wt % to about 30 wt %, about 10 wt % to about 20 wt %, about 20 wt % to about 90 wt %, about 30 wt % to about 90 wt %, about 40 wt % to about 90 wt %, about 50 wt % to about 90 wt %, about 60 wt % to about 90 wt %, about 70 wt % to about 90 wt %, about 80 wt % to about 90 wt %, about 20 wt % to about 80 wt %, about 30 wt % to about 80 wt %, about 40 wt % to about 80 wt %, or about 50 wt % to about 80 wt %, based upon the total amount of filler.

Fluorapatite:

The fluorapatite used herein is crystalline, and can have a nanorod shape. The crystals can have a length of about 500 nm to about 20 µm and a cross section of about 10 nm to about 3 µm. In some cases, the crystals have a length of about 500 to about 5 µm, or about 1 to about 2 µm. In various cases, the crystals have a cross section of about 10 to about 500 nm, about 10 to about 200 nm, about 20 to about 150 nm, about 20 to about 100 nm, about 20 to about 50 nm, or about 30 to about 40 nm. In other cases, the crystals have a cross section of about 2 to about 3 µm. In a specific case, the crystals have a length of about 500 nm to about 2 ti and a cross section of about 50 to about 500 nm. Methods of preparing apatite derivative crystals are known in the art, e.g., WO 06/050365, which is herein incorporated by reference in its entirety. Further contemplated are FA crystals having a cross section less than 2 µm are preferred, and crystals of less than 1 µm, less than 500 nm, less than 400 nm, less than 300 nm, less than 200 nm, or less than 100 nm. In some cases, the FA crystals are about 20 to about 50 nm in cross section.

Silica:

Precipitated silica can be included in the filler. In some cases, fumed silica (e.g., Aerosil 200) can be included in the filler. The silica can be silanized silica.

Composite Material:

Composite materials, consisting of inorganic particulate fillers dispersed in a cross-linked polymeric continuous phase, are well accepted and have significantly displaced amalgams as dental restorative materials owing to their improved aesthetic properties and the mercury-centered toxicity concerns associated with amalgams. These composite dental restoratives are typically processed in situ by photopolymerization whereby the filled monomeric resin is placed in the patient's mouth and irradiated with visible light, generating reactive species that initiate the polymerization and harden the material. Unfortunately, these polymerizations are typically accompanied by a significant amount of frustrated volumetric shrinkage and associated shrinkage stress, leading to a wide range of deleterious effects, including localized debonding and marginal gap formation, tooth deflection, and tooth cracking. Mitigation of this polymerization-induced shrinkage and/or the concomitant stress has been the focus of extensive research efforts over the past several decades and has been explored using an array of approaches, including low shrinkage ring-opening polymerization chemistries, modification of the in situ processing protocol, and polymerization-induced phase separation. Moreover, in clinical settings, the stress developed upon polymerization of these composite materials is not observable to practitioners; thus, the success and potential longevity of a photopolymerized composite restoration is impossible to accurately evaluate. Thus, provided herein is a concurrent thiol-ene-based polymerization and allyl sulfide-based addition-fragmentation chain transfer chemistries to afford cross-linked polymeric matrices that demonstrate both low shrinkage and low shrinkage stress. Additionally, incorporation of polymerizable mechanophores, mechanically-activated chromophores that manifest visible cues at raised stresses, in the polymeric continuous phase to allow practitioners to immediately assess dental restoration success.

Composite restorative materials have undergone many changes especially in the area of filler particle size; macro, micro, hybrid and nano sized particulate fillers have appeared and some have disappeared from the market. The percentage of particulate fill of a composite has been shown to influence its mechanical properties and polymerization shrinkage. The percentage of particle loading by volume ranges widely between 53% and 87% and the optimal particle load is influenced by several factors; shrinkage, mechanical properties, degradation etc. and clinically, the handling characteristics of the composite, an important factor in a composite's acceptance by the dental profession. A factor one cannot ignore when designing and developing a new composite restorative material. The size and shape of the filler particles also influence the % loading of the composite and its polishability. Particle sizes of 20 nm to over a micron; and shape from spherical to irregular have been reported in the literature. Although introducing apatite and fluoride containing compounds into a composite formulation is not a new concept, the incorporation of these biomimetic, enamel-like crystals is novel. These FA crystals, when used as coating, have been shown to be extremely bioactive causing: inhibition of pathogenic oral bacteria;

inhibiting carious lesion progression by releasing ions at low pH favoring remineralization; and stimulating dental pulp stem cells to mineralize which would aid in protecting the pulp in deep cavities. These biological effects make them ideal for incorporation into this novel polymer composite system. However, these bioactive advantages the FA crystals bring as a filler are predicated on surfaces coated with 100% FA crystals. The biological effects of the lesser amounts of unsilanated FA that will probably be incorporated into the polymer to produce the composite need to be evaluated. It may be that a mix of unsilanated FA crystals and silanated silica particles as the filler may be ideal to bring about the biological effects imparted by the FA crystals while maintaining stress relaxation and mechanical properties that exceed those of contemporary composites used in dental practice.

Discussion of Studies

Provided are the following objectives: To develop a biocompatible, low-air-inhibition, low shrinkage stress, self-reporting, inexpensive photopolymerizable thiol-ene-based resin that is able to relieve polymerization-induced shrinkage stress via rearrangement of the network connectivity, and that affords a transient, practitioner-observable warning if the shrinkage stress exceeds a pre-determined threshold. We will also test its mechanical properties benchmarked against other contemporarily used composite polymer systems; To optimize the silica filler only ratio (and then the FA to silica ratio) in the dental composite to ensure less than a 4% with an aim of approximately 1% volume shrinkage and meet or exceed the mechanical properties of contemporary composites; To establish the biocompatibility, antibacterial activity, enzymatic degradation of and, if appropriate, ion release at low pH from the optimized composite prototypes; To ensure bond strengths of the composite prototypes to enamel and dentin are at or exceed those reported for composites used in clinical dentistry today.

A base thiol-ene monomer solution is formulated by mixing thiol and ene monomers such that the ratio of thiol to ene functional groups is 1:1. While any combination of different thiol and ene monomers can be utilized, pentaerythritol tetra(3-mercaptopropionate) (PETMP), an odorless, low vapor pressure tetrathiol, is used in conjunction with a multi-functional allyl- or norbornyl-based co-monomer (see Scheme 1).

Scheme 1

A)

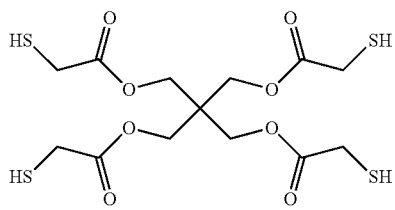

B)

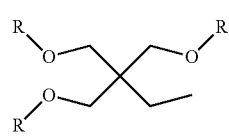

(i)

-continued

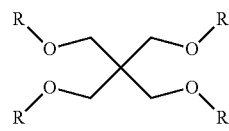

(ii)

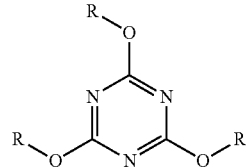

(iii)

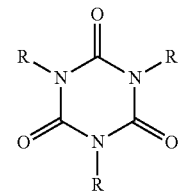

(iv)

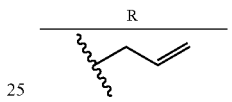

allyl

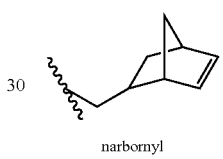

narbornyl

Structures of multifunctional thiol and ene co-monomers. (A) PETMP, a thiol monomer used herein. (B) The ene-based monomer cores, including (i) trimethylolpropane, (ii) pentaerythritol, (iii) triazine, and (iv) triazinetrione, will be functionalized with allyl and norbornyl polymerizable groups.

Whereas triallyl triazine trione and triallyl triazine are commercially available from Sigma-Aldrich, trimethylolpropane triallyl ether, pentaerythritol tetraallyl ether, and the norbornyl-functionalized monomers will be synthesized in-house according to known techniques. The thiol-ene solutions will be formulated with between 0.1 and 1.0 wt % bis(2,4,6-trimethylbenzoyl) phenyl phosphineoxide (BAPO, BASF) as a simple, highly efficient photoinitiator owing to its absorbance in the blue region of the spectrum. Formulations will be polymerized at both room temperature and at 37° C. using a light-emitting diode (LED)-based dental lamp that employs dual LEDs for photo initiators in the 390 to 460 nm wavelength range (SmartLite Max, Dentsply International). All eight formulations will be evaluated for polymerization kinetics and overall functional group conversion at 22 and 37° C. (procedure outlined in the FTIR Spectroscopy section), glass transition temperature and glassy modulus (procedure outlined in the Dynamic Mechanical Analysis section below), and shrinkage stress (procedure outlined in the Polymerization Shrinkage Tensometry section below). Parameters including photoinitiator concentration, irradiation intensity, and atmospheric oxygen concentration will be investigated. Samples comprising 70 wt % bisGMA/30 wt % TEGDMA (bisphenol A diglycidyl ether dimethacrylate and triethylene glycol dimethacrylate, respectively) are prepared and analyzed as benchmarks. A successful candidate resin exhibits a glass transition temperature of at least 60°

C., a modulus at 37° C. of at least 1 GPa, and polymerizes at least half as rapidly and generate at most 50% of the shrinkage stress developed by the model bisGMA/TEGDMA resin under equivalent reaction conditions. Previous work has demonstrated that PETMP/triallyl triazine trione and PETMP/triallyl triazine resins will exceed these specifications. Moreover, owing to trends observed elsewhere, it is anticipated that replacing the allyl functional group with norbornyl functionalities will raise the polymerization rate and increase the glass transition temperature and glassy modulus to yield at least two more candidate formulations that exceed the described specifications.

The four thiol-ene resins yield the highest glass transition temperatures and that also exceed the all of the described specifications will subsequently be formulated with 10, 20, and 40 wt % of the difunctional allyl sulfide ring opening monomers shown in Scheme 2.

Scheme 2

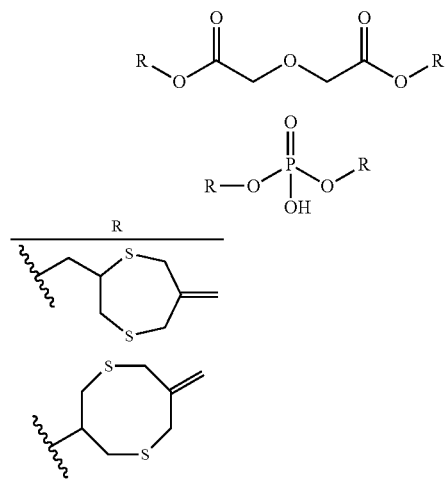

Structures of multi-functional, allyl sulfide ring opening monomers. The (i) diglycolate and (ii) phosphodiester monomer cores will be functionalized with 7- and 8-membered methylene-dithiacyclo polymerizable groups.

The inclusion of these monomers in the thiol-ene base resins allows for facile incorporation of the allyl sulfide functional group into the network backbone through which addition-fragmentation chain transfer can proceed, yielding a dramatic reduction in shrinkage stress. These allyl sulfide ring opening monomers do not alter the reaction stoichiometry of the thiol and ene functional groups and thus are particularly appropriate for incorporation in a base thiol-ene formulation. Moreover, upon ring opening and incorporation into the polymer network, these monomers introduce two cross-links and consequently will minimally affect the cross-link density and, in turn, the glass transition temperature of the fully-polymerized material. The allyl sulfide ring opening monomers will be synthesized using simple chemistry from readily available starting materials. Notably, the ring size and linker are the only aspects that differentiates these ring opening monomers. The 7-membered ring monomers are likely to exhibit faster polymerization kinetics owing to the increased ring strain relative to their 8-membered ring counterparts; however, upon polymerization, the resultant allyl sulfide from the 7-membered ring monomers may exhibit lowered stress relaxation rates and extents owing to steric hindrance. Whereas the diglycolate backbone will be inert in the composite restorative material, the analogous but acidic phosphodiester backbone impart self-etching/adhesion properties. The monomer formulations will be evaluated for polymerization kinetics, overall functional group conversion, percent leachable monomer as measured by FTIR Spectroscopy, and glass transition temperature and storage modulus. The candidate thiol-ene resins without the ring opening monomers and 70:30 bisGMA/TEGDMA will be prepared and similarly analyzed as benchmarks. Finally, the most promising thiol-ene-allyl sulfide resins will be assessed for biocompatibility.

During the studies examining the influence of the allyl sulfide incorporation on the polymerization kinetics, shrinkage stress and glass transition, diallylated spiropyran monomers will be synthesized by reaction of derivatized 2-methylene-1,3,3-trimethylindoline with corresponding methoxy- and nitro-benzaldehyde derivatives to generate a library of six 'push-pull' and 'pull-push' compounds, where the electron density is shifted towards the either the chromene/oxazine or indole moiety, by incorporating electron-withdrawing (EWG) and electron-donating groups (EDG) (see Scheme 3). As EWG and EDG substituents affect the stability of the colored, merocyanine isomer, the mechano-chemical stress sensitivity of the mechanophoric monomers can be finely tuned.

Scheme 3

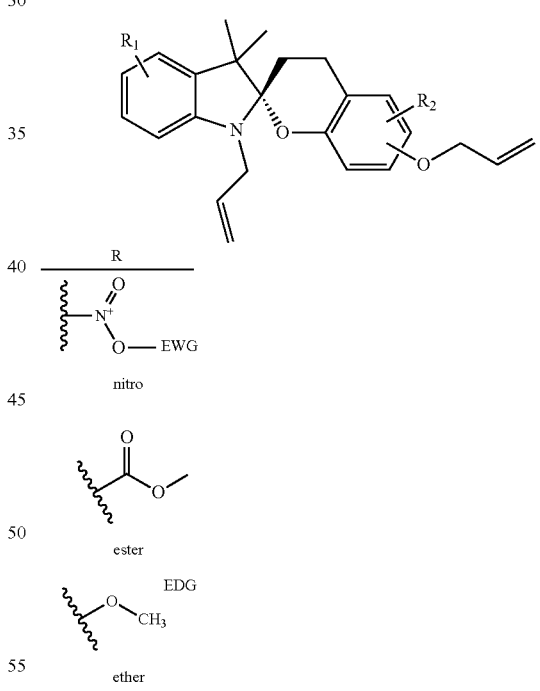

Spiropyran-based mechano-phoric diallylic monomer structures. R substituents ($R_1$ and $R_2$ in Scheme 3) include electron withdrawing and donating groups (EWG and EDG, respectively).

The synthesized spiroheterocyclic monomers will be incorporated in the candidate thiol-ene dental resin exhibiting the highest shrinkage stress and subject to photopolymerization using blue light to yield cross-linked polymers incorporating the spiro carbon in their backbone. Owing to the high visible light absorbance of the merocyanine isomer, resins will be formulated with a mechanophore loading of 0.1 wt %, thus the incorporation of mechanophoric monomers in the resin formulation will have a negligible effect on the ultimate mechanical properties. Formulations will be polymerized at ambient temperature and will be evaluated for polymerization kinetics and overall functional group conversion and mechanophore isomerization, and stress/isomerization state relationships will be determined. The high shrinkage stress that develops during the polymerization of these vitrifying resins will induce isomerization of the incorporated mechanophores, effecting a transient color change. The stress threshold for color development will be tuned by the utilization of the synthesized compound library described above. Mechanophore isomerization will be characterized as a function of the shrinkage stress and functional group conversion during photopolymerization using tensometry.

Fourier transform infrared (FTIR) Spectroscopy: Polymerization kinetics and overall functional group conversion will be determined by FTIR spectroscopy using a Nicolet 6700 FT-IR Spectrometer. The reaction progress will be monitored by measuring the functional group conversions as a function of polymerization time with either mid- or near-infrared spectroscopy. Infrared spectroscopy is well suited for rapid, in situ measurement of the photopolymerization kinetics, for independent measurement of multiple polymerizable functional group conversions, and for remote measurement, via fiber optic cables, of these while manipulating the sample in another apparatus. Polymerization kinetics samples are run in triplicate.

Polymerization Shrinkage Tensometry: The shrinkage stress generated during the photopolymerization of a resin is readily determined using an instrumented tensometer. This apparatus consists of a cantilever attached to a sturdy base. Affixed to the cantilever and base are two surface treated, co-aligned, quartz rods between which is a small gap. Photopolymerizable resin is positioned in this gap and irradiated via the lower quartz rod with a curing lamp, initiating the polymerization. As the polymerization proceeds, the stress associated with shrinkage deflects the cantilever; this deflection is monitored with a linear variable differential transformer, the data from which enables the determination of the shrinkage stress evolution.

Analogous to the concurrent stress and isomerization characterization described above, simultaneous shrinkage stress and functional group conversion measurements are collected by coupling an FTIR spectrometer via near-infrared transmitting optical fiber patch cables co-aligned on either side of the polymerizing sample in the plane transverse to the quartz rod axes. Similarly, coupling a UV-vis spectrometer, again via co-aligned UV-visible transmitting optical fiber patch cables positioned in the transverse plane but perpendicular to the IR optical fiber cables, allows the consumption of the photoinitiator and the isomerization of the incorporated mechanophores to be also monitored concurrently.

Ultraviolet-visible (UV-vis) Spectroscopy: Photoinitiator consumption and mechanophore isomerization will be determined by UV-vis spectroscopy using an Agilent Cary 60 UV-Vis Spectrophotometer. These reactions will be monitored by measuring sample absorbance from 350 to 700 nm. Analogous to FTIR spectroscopy, UV-vis spectroscopy is well suited for rapid, in situ measurement of the photoinitiator consumption and isomerization kinetics and for the remote measurement, via fiber optic cables, of these while manipulating samples in another apparatus, and experiments are run in triplicate.

Dynamic Mechanical Analysis (DMA): DMA is used to measure a number of relevant thermomechanical properties including polymer glass transition temperature (D, and glassy and rubbery storage and loss moduli. The DMA also allows for very sensitive measurement of the glass transition temperature of highly cross-linked materials. Double bond conversion measurements made via infrared spectroscopy before and after heating will be used to assure that no additional polymerization occurs during the measurement. These measurements will be performed using a TA Instruments Q800 DMA.

Fillers:

Provided herein are self-reporting composite resins, which can comprise fillers that influence the resin's shrinkage and other mechanical properties. There is a large range of filler volume percentages used in contemporary composites, from 53 to 87 vol %. In our composite formulation the vol % of the silica particles to load the polymer system are typically 55, 65, 75 and 85 vol % (e.g., about 55-85 vol %), to model the loads reported in clinically used composites. The particles of known size range and shape will be used in the formulation of the prototypes. These silica particles are silanated. It is conceivable that problems may arise during the formulation of the higher vol % prototypes and they have to be abandoned because silica particle dispersion and "wettability" are compromised. After the successful formulation of several prototypes (different vol % fills) with optimal particle dispersion and wetting of the particles, the shrinkage and mechanical properties of the composite will be measured. Cure time by photo-activation can be adjusted as necessary depending upon the exact components of the material. The prototypes that approximate 1% shrinkage by volume and are at or exceed the mechanical properties of contemporary used composites and cure in approximately 20 s, will passed to our clinical team to assess their handling characteristics. Based on their recommendation the refinement of the vol % silica fill and the cure time within smaller ranges are anticipated.

Some of the silica filler particles can be substituted with 10, 20, 30, and 40 vol % of unsilanated FA crystals. It has been discovered that up to 20 vol % of unsilanated FA crystals substituted for the silica particles in a bisGMA/TEGDMA/silica composite and did not compromise statistically its flexural strength or elastic modulus. Further, there is evidence of fluoride release from this same resin filled with unsilanated FA crystals (and less from silanated crystals, although the % fill for these crystals was smaller. Following the same protocol used for formulating and testing the experimental composite outlined above the optimal substitution of the FA crystals for the silica particles will be established. Our experimental composite benchmarks will be the target shrinkage, mechanical and handling parameters used above for the silica filled experimental composite. A contemporary and our experimental composite will be used as controls. Assuming this is successful the optimized FA/silica composite prototype(s) will undergo biological testing to assess their cellular biocompatibility, antibacterial activity and ion release characteristics. In order to ensure exposure of the FA, on which the biological and ion release activities depend, the optimally FA substituted composite will be polished, a standard clinical procedure after placement of a composite restoration. Polished and unpolished prototypes will be investigated for their biological and ion release properties.

Failing a biological response from the unsilanated FA/silica experimental resin we will test using silanated FA crystals which will allow a greater FA crystal fill and may still maintain the shrinkage, mechanical and handling parameter benchmarks of the silica only filled experimental composite. Again polishing of the silanated FA/silica experimental prototypes should expose the FA crystals allowing ion release and bioactivity.

Testing of Prototype Resin Samples for Clinical Handling Characteristics: The clinical group will assess for each experimental prototype resin the following properties: consistency, condensability, sculpt ability and adaptability to cavity walls. These will be subjective evaluations by two independent, experienced clinicians to determine the suitability of the material for ease of manipulation in a clinical situation, to establish a manageable placement technique with minimal air-void incorporation and to assess adaptation of the set material to prepared cavity walls. Appropriate instrumentation and prepared extracted teeth will be used for the procedures.

Mechanical Evaluation of Polymers and Composites: Mechanical properties (modulus, flexure strength, toughness and fatigue resistance) of the new polymers, as well as composites based on the new polymers, are evaluated. Mechanical evaluation will involve testing both the newly polymerized polymers as well as those aged for 90 days in the enzymatic solution and buffered lactic acid solution to demonstrate that the polymer does not undergo environmentally assisted mechanical degradation.

For the polymers, up to 2 processing temperatures×4 irradiation intensities×4 concentrations of initiator will be tested and baselined against neat BisGMA/TEGMA, BisGMA/TEGMA/UDMA and BisGMA/BisEMA/TEGMA supplied from Kerr. Initial tests will be geared toward assessing the feasibility of the polymers for use as composite matrices. The primary success criterion for screening of the polymers is a volumetric shrinkage of less than or equal to 8%. The subset of processing, irradiation and concentrations yielding polymers that meet the shrinkage criterion will be advanced to mechanical evaluation, and polymers with mechanical properties meeting or exceeding those of the existing acrylic resins noted above will be considered acceptable.

Composites will be formulated from the subset of 5 polymer conditions that best meet these success criteria. Initially, composites will be formulated with silica fillers, similar in size, composition and percentage to those used in the commercial composites we will benchmark against. Following evaluation of the composites containing polymer/commercial fillers, we will formulate composites containing 10, 20, 30 and 40 vol % unsilanated FA filler substituted for the silica. Properties of the new composites containing both types of fillers will be baselined against commercial composites from multiple manufacturers, which exhibit properties near the mean values noted below. Tetric EvoCeram (Ivoclar Vivadent), Prodigy (Kerr Corp.) and Filtek Supreme Ultra Universal Restorative (3M ESPE). Based on comprehensive data for over 70 commercial composites, properties vary by over a factor of 2 and variance is as high as 25% of the mean. A summation of the literature suggests that the range (and average) flexural strength, flexural modulus compressive strength and fracture toughness for composites (including hybrids, nanohybrids, microfilled and packable composites) are 75-160 (120) MPa; 2-13 (7) GPa; 140-280 (80) MPa and 0.5-2.0 (1.1) MPa/m$^2$. The primary outcome measure for the new polymers/composites will be polymerization shrinkage, but the target outcomes for the mechanical properties will be to meet or exceed the mean compressive, flexural and toughness properties of current composites and meet a fatigue criterion of ≤2% compliance loss at 2.5 million cycles.

Elastic Modulus:

Compression tests will be performed on an Instron 8521 servohydraulic mechanical testing machine, at a rate of 0.5 mm/min. Cylindrical specimens will be formed in a Teflon mold (8 mm×4 mm dia) covered with a Mylar strip and a glass slide. Top and bottom surfaces will be light cured, then the specimens will be taken out of the mold and light cured in the middle of the specimen on opposing sides. Following curing, specimens are placed between platens whose faces are well lubricated to minimize friction. Each specimen is cyclically preloaded between 0 and 25% of the estimated ultimate compressive load until the change in stiffness is less than 1% from the previous cycle (typically 5-10 cycles). Failure is determined by a drop in the load-displacement curve. The mechanical data are acquired directly on a PC, using a National Instruments data acquisition board and Instron software, and the ultimate stress, strain and stiffness are calculated.

Flexural Tests:

Flexural strength and modulus will be determined in 3-point bending. Polymer (or composite) specimens will be cured between glass plates, separated by a steel mould (2×2×16 mm). Curing will occur from both sides in a light-curing oven. After curing, specimens are removed from the mould, finished with 600-grit SiC paper to minimize surface voids. Specimens are loaded to failure in an Instron 8501 machine in a 3-point bending jig with 12-mm distance between the supports. Samples are loaded at a rate of 0.5 mm/min and kept immersed in distilled water. Force and deflection are monitored and bending modulus and flexural strength are calculated from the slope of the linear part of the force-deflection diagram and the maximum force and dimensions of the sample, respectively.

Toughness:

Specimens will be polymerized in Teflon molds to meet specimen geometries specified by the ASTM standard for plane strain fracture toughness testing. Notched 3-point bending specimens are used. Following curing, a 1 mm wide notch is machined into each specimen with a diamond saw. A groove is cut into the tip of the notch with a scalpel. A fatigue crack is propagated from this notch to create a standardized sharp crack in the sample. Prefatiguing will be performed on an Instron 8501 machine at a frequency of 1 Hz. Crack growth is monitored optically with a closed circuit video camera. When the fatigue crack propagates to a length of approximately 2 mm, the sample is removed from the machine and a colored dye is injected into the open notch to allow identification of the initial pre-crack length and to facilitate initial pre-crack measurements necessary for the fracture toughness measurements. Specimens are then loaded on the Instron, in stroke control, at a rate of 0.1 mm/sec until fracture occurs. Load-displacement data are recorded. The validity of each test, and the value of the fracture toughness is determined as described in the standard.

Fatigue:

Fatigue tests will be conducted to demonstrate that the newly formed polymers and composites are able to resist at least 5 years of occlusal loads. Assuming an average occlusal force on molars of 400-800 N and 500,000 occlusal cycles/yr, we will simulate 5 years of service by loading at 500 N to 2.5M cycles. The geometry of the fatigue samples is the same as for the fracture toughness samples. Cyclic loading tests are performed, on an Instron 8521 servohydraulic testing machine. Specimens are loaded at a frequency of 3 Hz until 2.5M cycles or failure, whichever occurs first. Mechanical data is acquired directly on a PC, using a National Instruments data acquisition board and Instron software. Compliance is continually monitored and assuming a low number of catastrophic failures, compliance drop will be the primary outcome used to assess the resistance to cyclic loading of the materials.

Sample Size Selection and Statistical Analyses:

Based on the statistical tests that will be noted below and using the standard deviations representative of dental composites (for composites chosen, maximum variances are 24.0 MPa, 1.4 GPa and 43.3 MPa for flexural modulus, flexural strength and compressive strength respectively) and expected differences of 15% to design an experiment of power=80% and significance level of 0.05, it was determined that 8, 6 and 10 samples/condition are needed to establish significance for flexural modulus, flexural strength and compressive strength respectively. Since variances as a percentage of the mean for toughness and fatigue are at least as high as for compressive strength, 10 samples/condition will also be used to assess these properties. It is assumed that a 15% difference in properties becomes clinically significant.

Unfilled and optimally filled silica and optimally filled FA/silica prototypes will be subjected to 90 days in a 4.5 pH buffered lactic acid solution at 37° C. The mechanical properties outlined above will then be retested and mass loss, change in volume and density will be measured.

Each property of the polymers is analyzed via a 2-way ANOVA with respect to processing temperature, irradiation intensity and initiator concentration. Significant differences are further investigated using a Tukey HSD test. Polymer properties are further analyzed via t-tests against the commercially available polymers. Each property of the composites is analyzed via an ANOVA with respect to filler % and properties are further analyzed via t-tests against the commercially composites.

The biocompatibility, antibacterial activity, enzymatic degradation and ion release properties at low pH of the compositions disclosed herein are assessed.

Biocompatibility and immuno-compatibility evaluation: After rigorous purification of the precursor monomers and initiators, the most promising mechanophoric monomer candidates will be incorporated in model cross-linked polymers and their biocompatibility assessed by seeding cells on the polymers and measuring cell viability, attachment, and metabolic activity. NIH 3T3 fibroblasts, which have been used as a model cell line for testing cytocompatibility of biomaterials, other cell lines will also be used, dental pulp stem cells (DPSCs) and human gingival fibroblasts (HGFs). These cells will be seeded independently on the material and cultured in growth media (Dulbecco's modified Eagle's medium with 10% fetal bovine serum (DMEM/FBS) for up to 7 days. Cell viability and attachment will be assessed using the LIVE/DEAD Viability/Cytotoxicity assay (Invitrogen) and counting attached and/or live cells using brightfield and fluorescent imaging on Day 3 and 7 in culture. Cell metabolic activity will be assessed using the colorimetric Vybrant Cell Metabolic Assay (Invitrogen).

Long-term biocompatibility due to leachable material will also be examined. Materials will be soaked in phosphate-buffered saline (PBS) for 1, 3, 6 and 12 months under sterile conditions. Plated cells will be cultured with this extract solution and their viability and metabolic activity measured and cytotoxicity assessed.

A foreign material in a biological system may invoke an immune response, leading to several complications. As a measure of immuno-compatibility, materials will be assessed by their capacity to stimulate cytokine production in the murine macrophage cell line, RAW264.7.

Biocompatibility is not expected to be an issue with the composites disclosed herein since each individual component of the composite will have been tested for biocompatibility. The combination will be tested for biocompatibility using the above methodology. To establish the biological effect of these composites, the differentiation and mineralization of DPSCs will be studied. Thus, the ALP staining and Alizarin red staining of the cells grown on the optimized composite surfaces will be investigated over a 1-6 week time period.

Antibacterial activity: These are relatively unsophisticated bacterial tests but serve to establish quickly whether there is any antibacterial activity of the FA/silica experimental composites against two oral pathogens. A biofilm/mixed flora model is also contemplated for testing of antibacterial activity.

The antibacterial properties of the FA crystal on the compositions disclosed herein are tested using *S. mutans* (NCTC 10449) and *P. gingivalis* (W50) individually to demonstrate anti caries and antiperiodontal disease activity. Polymer specimens without FA crystals are used as a control. The composite samples are sterilized in an Ultraviolet chamber, and the suspensions incubated at 37° C. in an anaerobic incubator (80% $N_2$, 10% $CO_2$, and 10% $H_2$ atmosphere) for 24 hours. The optical density at light wavelength of 540 nm (OD540) of the test suspension are assessed using a spectrophotometer.

Colony Forming Units (CFUs) Counting Method: After being incubated at 3° C. in an anaerobic incubator, the assay solution is removed, and the composite samples separately transferred into a bijou containing 2 mL of sterile RTF and vigorously vortexed for 1 minute to remove the adhering bacteria. The CFU/mL is then calculated. The assay solution is also inoculated to an agar plate to determine the number of viable bacteria remaining in solution.

Biodegradation experiments: The composites are prepared according to the protocol described above and stored dry at room temperature until ready for use. Before the biodegradation experiment, the samples are pre-incubated in D-PBS for 48 hours at 3° C. in order to remove as much of the unreacted leachable monomers as possible. Following this pre-incubation period, three cured pellets are placed in 2 mL sterile vials. Each vial represents one sample group. The total surface area of the samples for each of these groups is 2.26 $cm^2$. Each group is incubated at 37° C. and pH 7.0 in 1 mL of D-PBS or CE (0.01, 0.05, 0.1 or 1.0 units/mL) or PCE (0.01, 0.05, 0.1 and 1.0 units/mL). Previous studies have indicated that the non-specific esterase p-NPA activity measured within human saliva ranged between 0.09 and 0.26 units/mL with an average value of 0.2 units/mL, and for PCE-like activity it ranged from 0.004 to 0.018 units/mL with an average of 0.011 units/mL. Hence, the concentrations under study are physiologically within a relevant range.

Maintenance of the nominal enzyme activity in the incubation solutions is done with a replenishment schedule, consisting of 10 μL of concentrated enzyme solution added every 24 hours to maintain the active enzyme concentration level.

Product isolation with use high-performance liquid chromatography (HPLC) and spectrometry analysis of degradation products: The HPLC fractions containing individual degradation products are collected based on the start and end of the product peaks in the HPLC chromatograms.

Quantification of released biodegradation products: The incremental amounts of released degradation products is measured by taking the area under the peaks and converting them to mass/cm² of initial composite surface area using calibration curves derived for MA, TEGDMA, and bisHPPP.

Measurement of the fluoride, calcium and phosphorous ion release at low pH from the composite: Fluoride concentration is measured with the use of an Orion combination fluoride electrode. Calcium and phosphorous release are measured using a spectrophotometric color reaction. These measurements are carried out after automatically cycling the FA/silica filled experimental prototypes ×3 at pH 4.5 for half an hour at 4, 4, and 9.5 hour intervals, during these intervals the composites are immersed in an artificial saliva solution containing 0.1 ppm F at 37° C. Ion release is measured after 1 day, 1 week, 1 month and 3 months in the buffered lactic acid solutions.

The bond strengths of the composites disclosed herein to enamel and dentin are assessed and compared with other composites used.

Bond strength testing: Freshly extracted third molar teeth arestored in 1% sodium azide solution until testing. Each tooth will be sectioned perpendicular to the long axis of the tooth just below the dento-enamel junction and the exposed flat dentin surface wet ground, etched and bonded with experimental prototype. A cylindrical polytetrafluoroethylene mold is then positioned over the prepared surface and secured. The experimental resin will be placed into the mold and cured according to specified instructions. The mounted specimen will then be stored in 100% humidity at 37° C. for 24 hours. The mounted tooth and specimen will be placed in the Instron machine with the shear plane parallel to the testing device and the test run with loading at 0.5 mm/min until shear failure occurs. Maximum shear values are recorded as kg load; MPa units, means and standard deviations are calculated according to the number of specimens tested for a given prototype resin.

Bond strengths are not always a guarantee of clinical performance but the experimental prototype bond strengths should at least be comparable to those reported for contemporary composites being used in dental practice.

EXAMPLES

Figure 1:
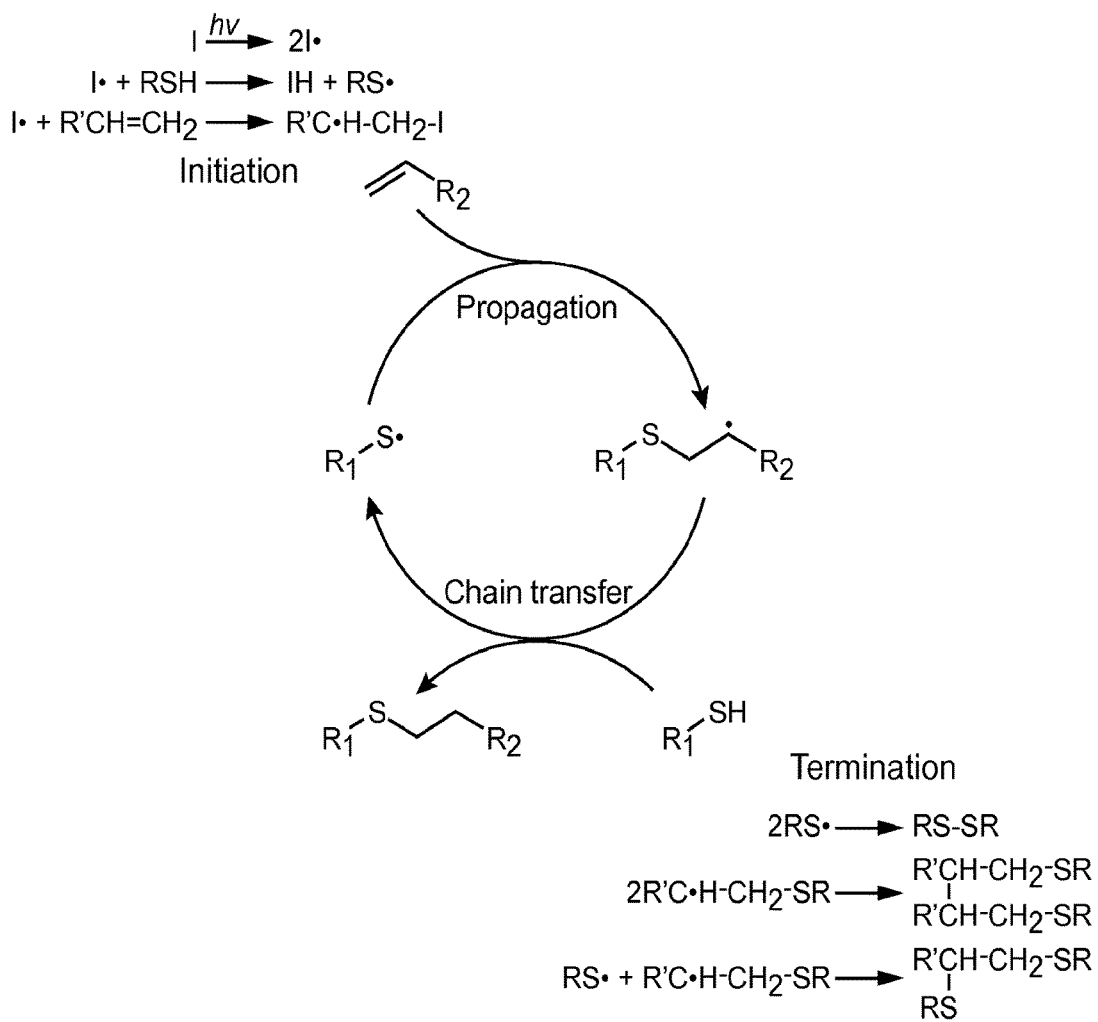
FIG. 1 shows the thiol-ene photopolymerization mechanism.
Figure 2:
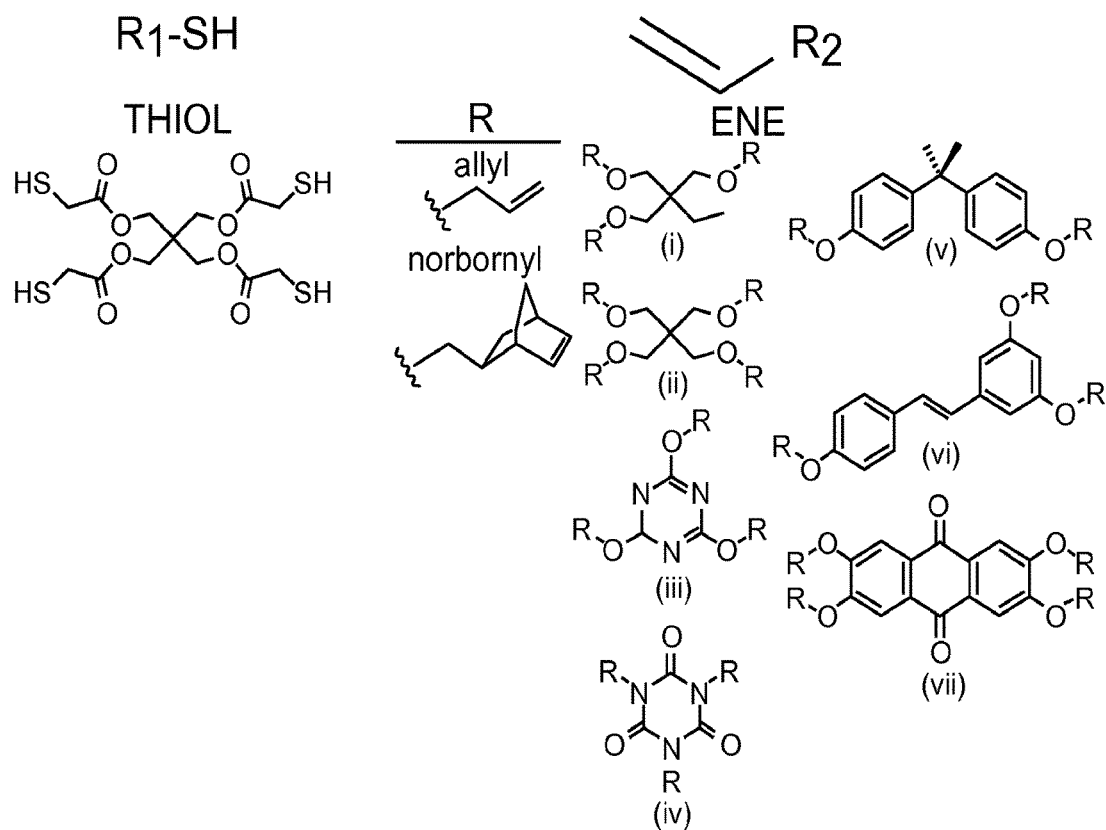
FIG. 2 shows various thiol-ene polymers that can be used for dental applications.
Figure 3:
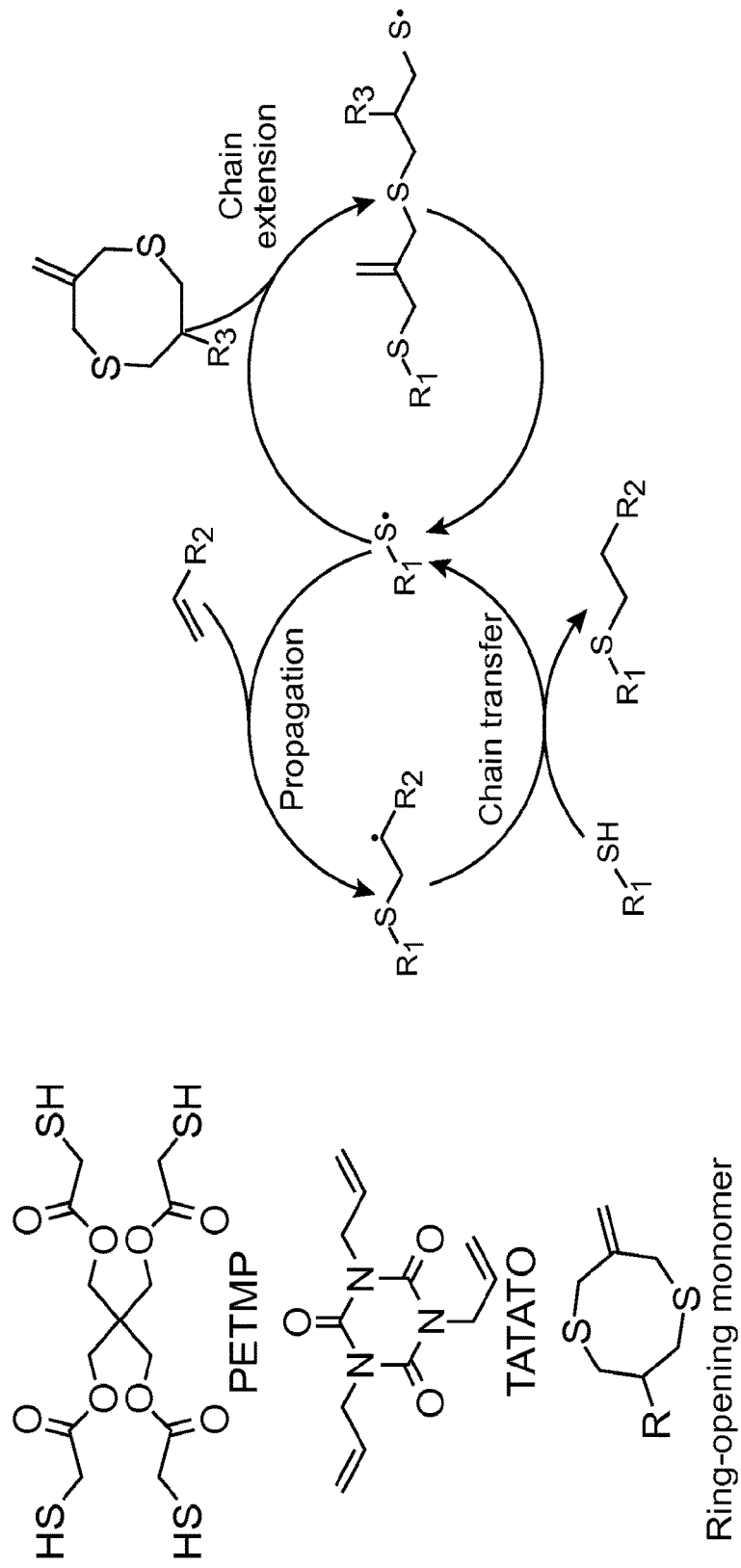
FIG. 3 shows use of allyl sulfide monomers incorporated into thiol-enes.
Figure 4:
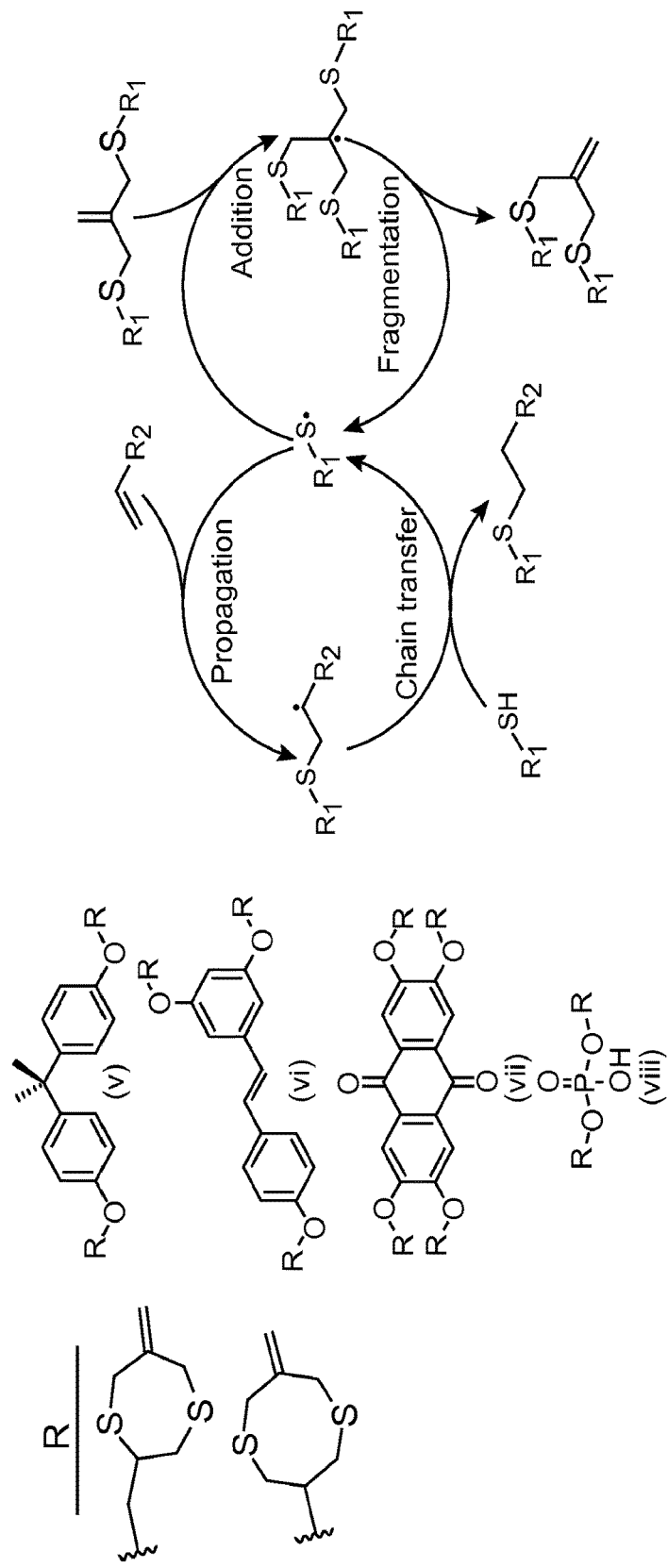
FIGS. 4 and 5 show concurrent thiol-ene polymerization and reversible addition/fragmentation chain transfer, and the resulting shrinkage/stress of the polymer.
Figure 5:
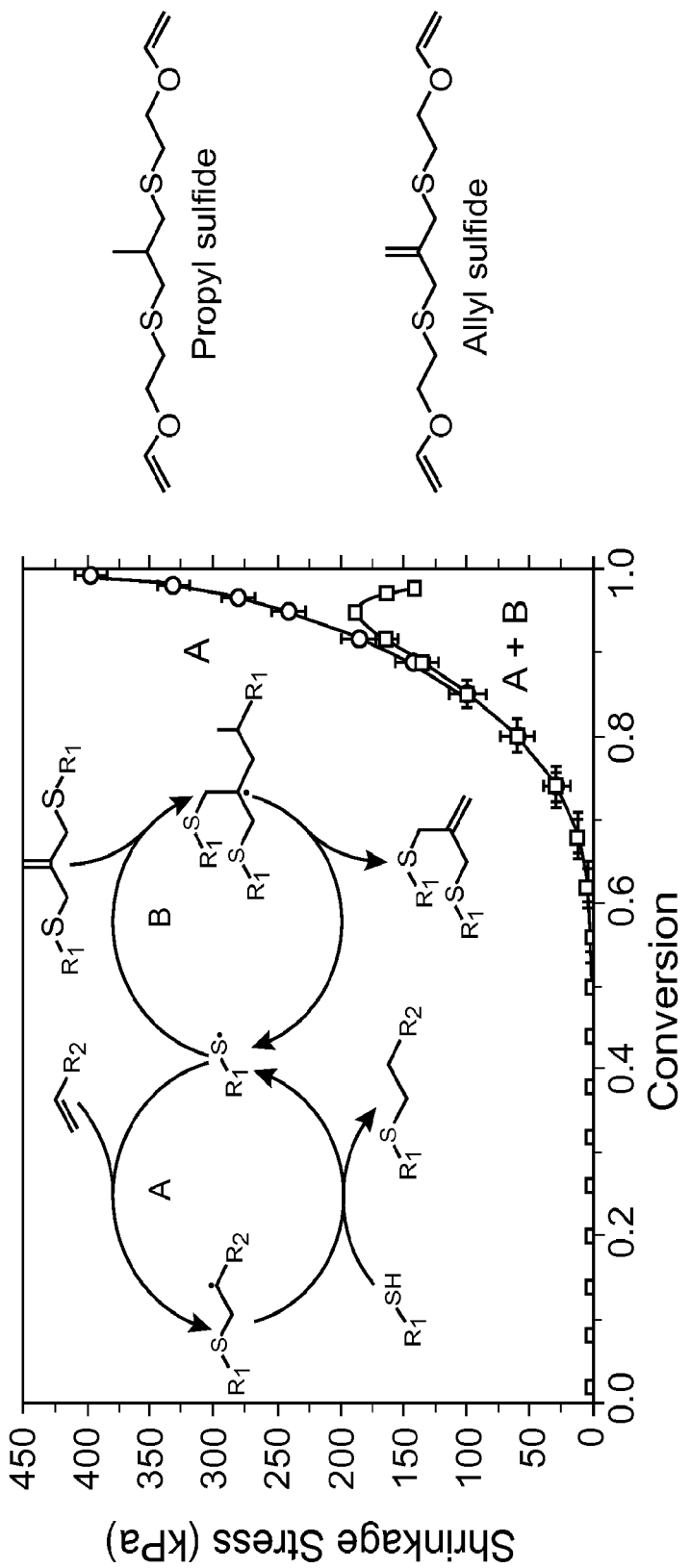

Stress Relaxation via Allyl Sulfide Addition-Fragmentation Chain Transfer: Shrinkage stress versus vinyl ether conversion ($p_{VE}$) for a 1:1 vinyl ether: thiol stoichiometric ratio of an allyl sulfide-incorporating PETMP/divinyl ether formulation (FIG. 5, triangles) and a negative control (FIG. 5, squares). The stress evolution for the allyl sulfide-containing material is markedly different than the negative control material, attributable to addition-fragmentation chain transfer through the network backbone which dominates the latter stages of the polymerization. Aside from the significantly reduced final stress, there is an apparent maximum and subsequent relaxation in the stress evolution.

Growth of Human Gingival Fibroblast (HGF) on FA Surfaces: —Cell attachment assay (FIG. 9, right) FIG. 9 shows the FA surfaces support the growth and proliferation of HGFs. There was no significant difference between the number of HGFs grown on control (SSE) and FA surfaces at day 1, 3 and day 14.

Cell cycle analysis showed a similar percentage of cells in "S" and "G₂M" phases. No significant difference of proliferation index (PrI, S+G₂M) of the cells was found between two groups (p>0.05).

Fluoride release (ppm) from FA crystals): Table 1 shows the fluoride release under varying pHs and times from the FA crystal coated discs. The first measurement for all groups independent of pH shows considerable fluoride release. However after the initial 30 minutes it was shown that fluoride release occurred at pH<5 but not at pHs 7 or 6. Therefore the fluoride release measurements over the 10 day experimental period were carried out at pHs 4.5 and 4.0 to ensure fluoride release at the acidified gel pH of 4.3. The average fluoride release of groups 3 and 4 was 0.16 ppm/cm² per acid exposure. *NM=not measured

TABLE 1

| Time of Reading | Group 1 pH = 7 | Group 2 pH = 6 | Group 3 pH = 4.5 | Group 4 pH = 4 |
|---|---|---|---|---|
| 0.5 hrs | 3.2 | 2.34 | 3.2 | 3.37 |
| 4.5 hrs | 0 | 0 | 0.62 | 0.26 |
| 24.5 hrs | 0 | 0 | 0.39 | 0.78 |
| Day 5 | NM | NM | 0.56 | 1.01 |
| Day 10 | NM | NM | 0.79 | 0.50 |

Figure 13:
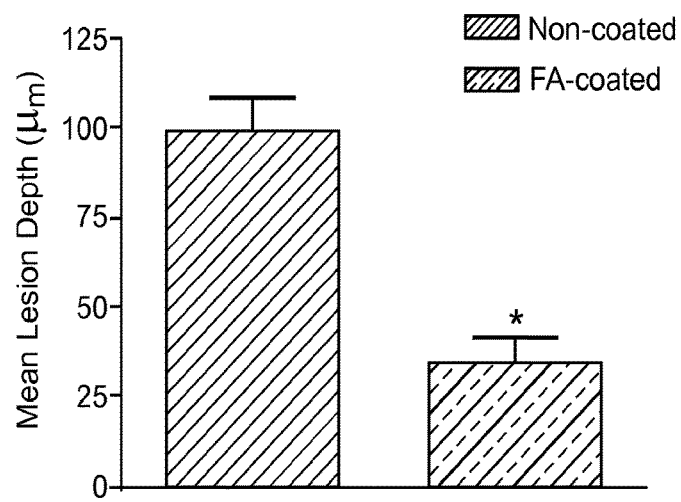
FIG. 13 shows the lesion depths in enamel for fluorapatite (FA)-coated vs. non-FA coated stainless steel crowns.

FIG. 13 shows the mean depths of the acid gel induced lesions. Teeth were sectioned through the lesions developed at the tooth/crown interface. Lesions into enamel were measured on each tooth section at two sites, the buccal and lingual surfaces. Lesions depth after 9 weeks of exposure to the acidified gel was approximately 4× less for the FA coated crowns versus the non coated crowns.

Fluoride release from FA containing composites are shown in Table 2. Table 2 shows fluoride release from composite of different filler vol. percentage (%) containing unsilanated or silanated FA crystals over 1 month time period. Considerable amount of fluoride release were detected from both silanated and unsilanated FA groups, however much higher fluoride release occurred in unsilanated FA group at all the three time points.

TABLE 2

| Composite | 1 day F, ppm | 1 wk F, ppm | 1 mo F, ppm |
|---|---|---|---|
| bisGMA/TEGDMA with 75% silanated silica | 0.07 | 0.08 | 0.06 |
| bisGMA/TEGDMA w/ 63% unsilanated FA | 0.8 | 2.1 | 1.3 |
| bisGMA/TEGDMA w/ 42% silanated silica & 20% silanated FA | 0.1 | 0.3 | 0.5 |

Composite flexural strength measurement: Table 3 shows the flexural strength, elastic modulus and (%) of the composite consisting of bis-GMA/TEGDMA resin filled with silanated silica particles and nonsilanated FA (NSFA) crystals. No statistical difference was found between the experimental groups.

TABLE 3

| Composite fill (%) | Flexural Strength (MPa) | Elastic Modulus (GPa) |
|---|---|---|
| 0 (silica only) | 126 ± 26 | 6.4 ± 1.9 |
| 10 (NSFA) | 90 ± 23 | 8.9 ± 4.0 |
| 20 (NSFA) | 118 ± 22 | 7.8 ± 2.7 |

Figure 14:
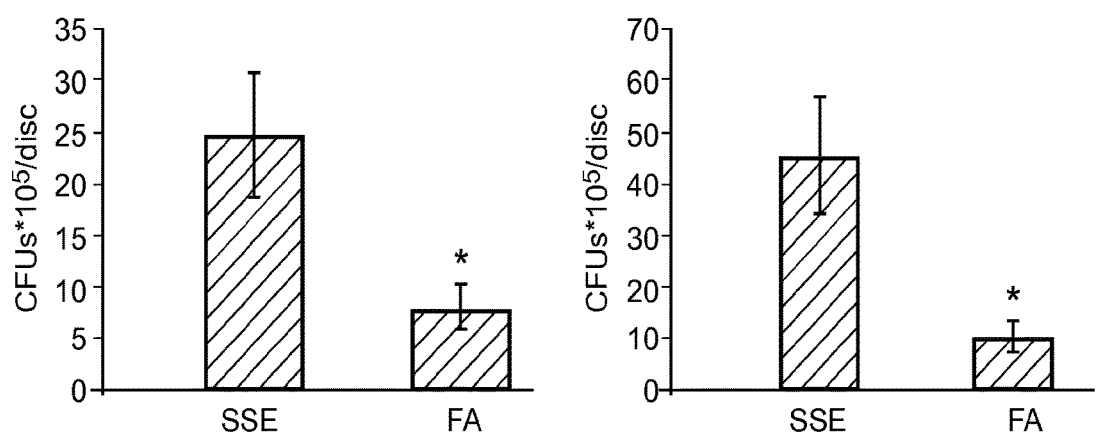
FIG. 14 shows the antibacterial properties of fluorapatite crystals, CFU counts of *P. gingivalis* (left) and *F. nucleatum* (right) grown on naked etched stainless steel (SSE) and FA coated SSE surfaces.

Antibacterial Test of FA crystals results are shown in FIG. 14 for colony forming units (CFUs) formation. FIG. 14 shows the antimicrobial behavior of a FA coated and the non-coated stainless steel (SSE) disc (control) against *S. mutans* (A) and *P. Gingivalis* (B) by colony forming units (CFUs) counting method (*signifies a statistical significance p<0.05). CFUs were reduced by the FA coating by a factor of approximately 5× (A) and 3× (B) when compared to the controls.

Polymerization at room temperature of various monomers is shown in Table 4 (room temperature), Table 5 (37° C.), with the intensity of 405 nm light used for irradiation noted in parenthesis.

TABLE 4

| | Polymerization at room temperature | | | | | |
|---|---|---|---|---|---|---|
| | First scan | | | Second scan | | |
| | E' at 23° C. (GPa) | E' at 200° C. (MPa) | $T_g$ (° C.) | E' at 23° C. (GPa) | E' at 200° C. (MPa) | $T_g$ (° C.) |
| PETMP/TATATO (1 mw/cm²) | 2.5 | 23.4 | 47.2 | 2.4 | 37.4 | 66.4 |
| PETMA/TATATO (1 mw/cm²) | 3.3 | 21.7 | 48.1 | 3.2 | 34.7 | 77.6 |
| TMES/TATATO (1 mw/cm²) | 2.1 | 48.4 | 83.7 | 1.9 | 50.3 | 106.9 |
| TMPS/TATATO (10 mw/cm²) | 2.0 | 58.5 | 63.1 | 1.8 | 63.4 | 83.7 |
| PETMP/DABPA (1 mW/cm²) | 0.27 | 4.52 | 26.61 | 1.47 | 9.45 | 34.21 |
| TMES/DABPA (1 mw/cm²) | 1.38 | 7.91 | 37.36 | 0.05 | 0.31 | 51.59 |
| TMPS/DATCB (10 mW/cm²) | | | below 0 | | | |
| TMES/DNBPA/TATATO (1 mw/cm²) | 2.2 | 24.0 | 73.4 | 1.9 | 23.2 | 104.9 |
| TMES/DNTCB/TATATO (1 mw/cm²) | 1.6 | 19.6 | 45.4 | 2.0 | 18.8 | 81.1 |

TABLE 5

| | Polymerization at 37° C. | | | | | |
|---|---|---|---|---|---|---|
| | First scan | | | Second scan | | |
| | E' at 23° C. (GPa) | E' at 200° C. (MPa) | $T_g$ (° C.) | E' at 23° C. (GPa) | E' at 200° C. (MPa) | $T_g$ (° C.) |
| PETMP/TATATO (1 mw/cm²) | 2.5 | 34.5 | 54.0 | 2.4 | 36.6 | 66.2 |
| PETMA/TATATO (1 mw/cm²) | 3.3 | 23.7 | 54.1 | 3.1 | 32.8 | 78.2 |
| TMES/TATATO (1 mw/cm²) | 2.2 | 52.5 | 103.1 | 2.0 | 55.8 | 112.5 |
| TMPS/TATATO (10 mw/cm²) | 2.1 | 60.9 | 68.2 | 1.9 | 68.4 | 83.6 |
| PETMP/DABPA (1 mW/cm²) | | | | | | |
| TMES/DABPA (1 mw/cm²) | | | | | | |
| TMPS/DATCB (10 mW/cm²) | | | | | | |
| TMES/DNBPA/TATATO (1 mw/cm²) | 2.3 | 25.1 | 76.2 | 2 | 22.9 | 107.2 |
| TMES/DNTCB/TATATO (1 mw/cm²) | 1.7 | 14.5 | 47.0 | 2 | 15.4 | 83.3 |

What is claimed:

1. A dental composite material comprising a resin and a filler, wherein the resin comprises a thiol-ene polymer and optionally a spiropyran, and the filler comprises fluorapatite (FA) crystals and silica,
    wherein the thiol-ene polymer is formed from a reaction mixture comprising (a) tetramercaptoethylsilane (TMES) and triallyltriazinetrione (TATATO); (b) tetramercaptopropylsilane (IMPS) and TATATO; (c) TMES/TATATO/dinorbornyl bisphenol A (DNBPA); or (d) TMES/TATATO/dinorbornyl tetramethyl cyclobutane (DNTCB).

2. The dental composite of claim 1, wherein the reaction mixture further comprises a photoinitiator.

3. The dental composite material of claim 1, wherein the reaction mixture further comprises an allyl sulfide.

4. The dental composite material of claim 1, comprising the spiropyran.

5. The dental composite material of claim 4, wherein the spiropyran is present in an amount of about 0.01 wt % to about 10 wt %, based upon the total weight of the resin.

6. The dental composite material of claim 1, wherein the filler comprises FA crystals having a length of about 500 nm to about 20 μm and a cross section of about 10 nm to about 500 nm.

7. The dental composite material of claim 1, wherein the FA crystals have a length of about 300 nm to about 750 nm and a cross section of about 50 nm to about 500 nm.

8. The dental composite material of claim 1, wherein the FA crystals are present in the composite in an amount of about 10 wt % to about 90 wt %, based upon the total weight of the filler.

9. The dental composite material of claim 1, wherein the silica is silanized silica or precipitated or fumed silica.

10. The dental composite material of claim 1 having a shrinkage volume of the thiol-ene resin of less than 8% vol.

11. The dental composite material of claim 1 having a shrinkage volume of the composite of less than 4% vol.

12. A method comprising applying the dental composite material of claim 1 onto a tooth surface.

13. The method of claim 12, wherein the FA crystal, after application to the tooth surface, dissolves or partially dissolves and releases one or more ions selected from the group consisting of fluoride, phosphate, carbonate, and calcium.

14. The method of claim 12, wherein the application of the dental composite material prevents or retards dental caries.

15. The method of claim 12, wherein the application of the dental composite material prevents or reduces tooth sensitivity.

16. The dental composite material of claim 1 for use as a lining material, bonding agent, or sealant.

* * * * *